(12) United States Patent
Loumaye et al.

(10) Patent No.: US 10,441,593 B2
(45) Date of Patent: Oct. 15, 2019

(54) TREATMENT OF PAIN ASSOCIATED WITH DISLOCATION OF ENDOMETRIUM

(75) Inventors: Ernest Loumaye, Cologny (CH); Elke Bestel, Saint-Julien-en-Genevois (FR); Ian Osterloh, Kent (GB)

(73) Assignee: PREGLEM S.A. (CH)

( * ) Notice: Subject to any disclaimer, the term of this patent is extended or adjusted under 35 U.S.C. 154(b) by 409 days.

(21) Appl. No.: 13/976,895

(22) PCT Filed: Dec. 23, 2011

(86) PCT No.: PCT/IB2011/055941
§ 371 (c)(1),
(2), (4) Date: Jun. 27, 2013

(87) PCT Pub. No.: WO2012/090143
PCT Pub. Date: Jul. 5, 2012

(65) Prior Publication Data
US 2013/0281422 A1    Oct. 24, 2013

Related U.S. Application Data

(60) Provisional application No. 61/457,107, filed on Dec. 30, 2010.

(30) Foreign Application Priority Data

Dec. 30, 2010  (EP) .................................... 10197400

(51) Int. Cl.
*A61K 31/57* (2006.01)
(52) U.S. Cl.
CPC .................................. *A61K 31/57* (2013.01)
(58) Field of Classification Search
CPC ....................................................... A61K 31/57
USPC .......................................................... 514/182
See application file for complete search history.

(56) References Cited

U.S. PATENT DOCUMENTS

| 4,954,490 | A | 9/1990 | Cook et al. |
| 5,073,548 | A | 12/1991 | Cook et al. |
| 5,929,262 | A | 7/1999 | Kim et al. |
| 6,900,193 | B1 | 5/2005 | Kim et al. |
| 8,173,626 | B2 * | 5/2012 | Hausknecht ......... A61K 31/557 514/179 |
| 8,299,050 | B2 | 10/2012 | Nieman et al. |
| 8,426,392 | B2 * | 4/2013 | Gainer et al. ................ 514/170 |
| 8,569,274 | B2 * | 10/2013 | Fauser ................. A61K 31/567 514/172 |
| 8,777,014 | B2 | 7/2014 | Chakroun |
| 2005/0085453 | A1 * | 4/2005 | Govindarajan ........ A61K 31/57 514/177 |

FOREIGN PATENT DOCUMENTS

| WO | WO 2004/065405 A1 | 8/2004 |
| WO | WO 2004/078709 A2 | 9/2004 |
| WO | WO 2007/103510 A2 | 9/2007 |
| WO | WO 2008/067086 A2 | 6/2008 |
| WO | WO 2009/134718 A1 | 11/2009 |
| WO | WO 2010/061065 A1 | 6/2010 |
| WO | WO 2010/066749 A2 | 6/2010 |

OTHER PUBLICATIONS

Gainer et al. Pharmacologic properties of CDB(VA)-2914. Steroids 68 (2003) pp. 1005-1011.*
Attardi, B.J., et al., "In vitro Antiprogestational/antiglucocorticoid Activity and Progestin and Glucocorticoid Receptor Binding of the Putative Metabolites and Synthetic Derivatives of CDB-2914, CBD-4124, and Mifepristone," *Journal of Steroid Biochemistry & Molecular Biology* 88:277-288, Elsevier Ltd., England (2004).
Blithe, D. L., et al., "Development of the Selective Progesterone Receptor Modulator CDB-2914 for Clinical Indications," *Steroids* 68:1013-17, Elsevier Inc., United States (2003).
Langer, R., "New Methods of Drug Delivery," *Science* 249:1527-1533, American Association for the Advancement of Science, United States (1990).
Templeman, C., et al., "Adenomyosis and Endometriosis in the California Teachers Study: Reproductive and Lifestyle Correlates," *Fertility and Sterility* 90(2):415-430, Elsevier for the American Society for Reproductive Medicine, United Statess (2008).
Vavilis, D., et al., "Adenomyosis at hysterectomy: prevalence and relationship to operative findings and reproductive and menstrual factors," *Clinical and Experimental Obstetrics & Gynecology* 24(1):36-38, Padova, Italy (1997).
Vercellini, P., et al., "Adenomyosis: epidemiological factors," *Best Practice & Research Clinical Obstetrics & Gynaecology* 20(4): 465-477, Elsevier Ltd., England (2006).
Chwalisz et al., "Treatment of endometriosis with the novel selective progesterone receptor modulator (SPRM) asoprisnil," abstract O-207, *Fertility & Sterility* 82(suppl 2):S83-S84, American Society for Reproductive Medicine, United States (2004).
Dance With Shadows, "PregLem's oral drug Ulipristal (Esmya) more effective to treat fibroids in uterus," May 20, 2010, accessed at http://www.dancewithshadows.com/pillscribe/preglems-oral-drug-ulipristal-esmya-more-effective-to-treat-fibroids-in-uterus/, accessed on Apr. 1, 2016.
Leyendecker, G., et al., "The pathophysiology of endometriosis and adenomyosis: tissue injury and repair," *Arch Gynecol Obstet* 280:529-538, Springer, Germany (2009).
Leyendecker, G., "Endometriosis results from the dislocation of basal endometrium," *Human Reproduction* 17(10):2725-2736, European Society of Human Reproduction and Embryology, Belgium (2002).
Repros Therapeutics Inc, "Repros Therapeutics Inc. Provides Additional Information on Proellex Clinical Program," Jul. 7, 2009, accessed through Thomson Reuters Cortellis.
Repros Therapeutics Inc, "Repros Therapeutics Inc. Suspends Dosing of Proellex and Provides Update on Financial Status," Aug. 3, 2009, accessed through Thomson Reuters Cortellis.

(Continued)

*Primary Examiner* — Jennifer M Kim
(74) *Attorney, Agent, or Firm* — Sterne, Kessler, Goldstein & Fox P.L.L.C.

(57) ABSTRACT

The present invention relates generally to gynecological diseases and in particular to a method for reducing pain associated with dislocation of basal endometrium.

7 Claims, No Drawings

(56) References Cited

OTHER PUBLICATIONS

Signorile, P.G., "Ectopic endometrium in human foetuses is a common event and sustains the theory of müllerianosis in the pathogenesis of endometriosis, a disease that predisposes to cancer," *Journal of Experimental & Clinical Cancer Research* 28:49, BioMed Central, England (2009).

Spitz, I.M., "Clinical utility of progesterone receptor modulators and their effect on the endometrium," *Current Opinion in Obstetrics and Gynecology* 21:318-324, Lippincott Williams & Wilkins, United States (2009).

Practice Bulletin titled "Management of Endometriosis" *Clinical Management Guidelines for Obstetrician-Gynecologists, Obstetrics & Gynecology*, 116(1):223-236, The American College of Obstetricians and Gynecologists, Women's Health Care Physicians (Jul. 2010).

Cullen, A., "Schering. TAP Halt Trial of Drug for Uterine Growths (Update5)," *Bloomberg*, dated Oct. 12, 2005. accessed from http://www.bloomberg.com/apps/news?pid=21070001&sid=afzw6ILGtTbE on Feb. 3, 2012.

Colca, J.R., "Discontinued drug in 2007: renal, endocrine and metabolic drugs," *Expert Opin. Invest. Drugs*, 17(11):1641-1550, Informa UK Ltd. (2008).

"Repros Therapeutics Inc. Suspends Dosing of Proellex® and Provides Update on Financial Status," *Business Wire*, dated Aug. 3, 2009, accessed from http://www.businesswire.com/news/home/20090803005407/en/Repros-Therapeutics-Suspends-Dosing-Proellex%C2%AE-Update-Financial on Jun. 29, 2017.

Report for "Safety and Efficacy Study to Evaluate Proellex in the Treatment of Premenopausal Women With Symptomatic Endometriosis," *ClinicalTrials.gov*, study completion date Jul. 2009, accessed from https://clinicaltrials.gov/ct2/show/NCT00556075?term=endometriosis&rank=83 on Jun. 1, 2017.

\* cited by examiner

US 10,441,593 B2

TREATMENT OF PAIN ASSOCIATED WITH DISLOCATION OF ENDOMETRIUM

TECHNICAL FIELD

The present invention relates generally to gynecological diseases and in particular to a method for reducing pain associated with dislocation of basal endometrium.

BACKGROUND OF THE INVENTION

Endometriosis and adenomyosis are often regarded as variants of the same condition, i.e. dislocation of basal endometrium, but are distinct gynecological condition.

Adenomyosis, also known as endometriosis interna, is characterized by the presence of ectopic glandular tissue found in muscle. It usually refers to ectopic endometrial tissue (the inner lining of the uterus) within the myometrium (the thick, muscular layer of the uterus). The condition is typically found in women between the ages of 35 and 50. Patients with adenomyosis can have painful and/or profuse menses. However, because the endometrial glands are trapped in the myometrium, it is possible to have increased pain without increased bleeding. In adenomyosis, basal endometrium penetrates into hyperplastic myometrial fibers. Therefore, unlike functional layer, basal layer does not undergo typical cyclic changes with menstrual cycle.

Endometriosis is characterized by the presence of endometrium-like tissue outside the uterus cavity, most frequently in the peritoneal cavity. Endometriosis almost exclusively affects pre-menopausal women and is a highly prevalent and highly underdiagnosed condition. There are an estimated 7 million endometriosis patients in the U.S., 12-14 million endometriosis patients in Europe and estimated 80 million in the rest of world. Endometriosis is a major cause of chronic pelvic pain, dyspareunia and sub-fertility. The condition is typically found in women between the ages of 15 and 50.

When analgesics like cyclo-oxygenase-2 inhibitors are not efficacious, treatments for endometriosis currently aim at reducing or suppressing menstruation and oestrogen production by the ovary. This is achieved by danazol, progestins, oral contraceptive pills or GnRH agonists. There are, however, many side effects, e.g. the use of GnRH agonists is limited to 6 months because of potential adverse effects on bone mineral density and treatment with danazol is also limited because of its androgenic side-effects. Moreover, in patients responding to treatment with GnRH agonists, symptom recurrence is reported in a majority of the patients within 5 years of treatment cessation.

The pain associated with endometriosis is the most difficult symptom to cope with for most women. For many, the pain they suffer severely interferes with every day life. It can be constant or it can be cyclical and coincide with a woman's period.

Recently, International Patent Application WO 2009/134718A1 (Repros Therapeutics) disclosed a method for treating an estrogen dependent condition comprising administering to a female in need thereof, a composition comprising an effective amount of a progesterone antagonist for an administration period beginning during the luteal phase of said female's menstrual cycle, wherein the endometrium of said female is not substantially thickened during said period. Endometriosis is listed as one of the numerous possible estrogen conditions.

This document also discloses a method for treating pain associated with, e.g. endometriosis wherein the progesterone antagonist is CDB4124 (Proellex®).

This document also shows the results of a 6 month study of Proellex® effect in the treatment of endometriosis. It is disclosed that "these results clearly support a dose response for CDB4124" and furthermore that "at the end of the first months of therapy, there was a statistically significant reduction in days of pain in the 50 mg Proellex group compared with baseline, but not in the three other treatment groups" (control group, Proellex 12.5 mg and Proellex 25 mg).

However, during Proellex'® clinical development program a dose related increase in liver enzyme (sign of liver toxicity i.e. Drug Induced Liver Injury [DILI]) has been observed when said drug was administered. (Press release published on Jul. 7, 2009 "Repros Therapeutics Inc. Provides Additional Information on Proellex Clinical Program"). As a consequence FDA decision was made to discontinue with Proellex® 12.5 mg, 25 mg and 50 mg (Press release dated Aug. 3, 2009 "Repros Therapeutics Inc. Suspends dosing of Proellex® and provides Update on Financial Status").

For the moment no fully optimal treatment against pain associated with endometriosis or adenomyosis is currently available. The pharmaceutical products currently used namely non-steroidal anti-inflammatory drugs (NSAIDS) and hormonal treatments like danazol, progestins or GnRH agonists, alleviate pain symptoms in only less than half of the patients.

Thus, there remain significant unmet needs for efficient, safe and better long term therapies for treating pain associated with endometriosis or adenomyosis.

SUMMARY OF THE INVENTION

The present invention provides an improved and reliable method for reducing pain associated dislocation of the endometrium, wherein said ulipristal, or said metabolite thereof, is administered at a daily dosage at a therapeutically effective amount of 5 mg to 12 mg.

The present invention provides an improved and reliable method for reducing pain associated with adenomyosis, wherein said ulipristal, or said metabolite thereof, is administered at a daily dosage at a therapeutically effective amount of 5 mg to 12 mg.

Also disclosed is a method for reducing or stopping bleeding in a patient afflicted with adenomyosis comprising administering to said patient in need thereof, a daily dosage of 5 mg to 12 mg of ulipristal, or any metabolite thereof.

Further disclosed is a method for preventing or treating anemia in a patient afflicted with adenomyosis, comprising administering to said patient in need thereof, a daily dosage of 5 mg to 12 mg of ulipristal, or any metabolite thereof.

The invention further provides a method for reducing uterine volume in a patient afflicted with adenomysosis, comprising administering to said patient in need thereof, a daily dosage of 5 mg to 12 mg of ulipristal, or any metabolite thereof.

The present invention provides an improved and reliable method for reducing pain associated with endometriosis comprising administering to a patient in need thereof a daily dosage of 5 mg to 12 mg of ulipristal, or any metabolite thereof.

Also disclosed is a method for reducing or stopping bleeding in a patient afflicted with endometriosis comprising administering to said patient in need thereof, a daily dosage of 5 mg to 12 mg of ulipristal, or any metabolite thereof.

Further disclosed is a method for preventing or treating anemia in a patient afflicted with endometriosis, comprising administering to said patient in need thereof, a daily dosage of 5 mg to 12 mg of ulipristal, or any metabolite thereof.

DETAILED DESCRIPTION OF THE INVENTION

As used herein, "dislocation of basal endometrium" refers to the displacement of the endometrium from its normal position—the lining of the uterus cavity—outside this position, i.e either to positions where the endometrial tissue is found inside the uterine myometrium (adenomyosis) or outside the uterus (endometriosis).

As used herein, the term "Endometriosis" refers to a condition characterized by the presence of endometrium-like tissue (glands and stroma) outside the uterus cavity, most frequently in the peritoneal cavity. Endometrium almost exclusively affects women in their reproductive years. Endometriosis is a highly prevalent and highly under-diagnosed condition. There are an estimated 7 million endometriosis patients in the U.S., 12-14 million endometriosis patients in Europe and estimated 80 million in the Rest of World. Endometriosis is a major cause of chronic pelvic pain, dyspareunia and sub-fertility. Proliferation and growth of endometrial tissue is estrogen-dependant.

Dislocation of the basal endometrium is also shown in women affected by "adenomyosis". This latter condition, also known as endometriosis interna, is characterized by the presence of ectopic glandular tissue in uterine muscle (i.e. myometrium). As already discussed supra, patients with adenomyosis can have painful and/or profuse menses. However, because the endometrial glands can be trapped in the myometrium, it is possible to have increased pain without increased bleeding. In adenomyosis, basal endometrium penetrates into hyperplastic myometrial fibers. Therefore, unlike functional layer, basal layer does not undergo typical cyclic changes with menstrual cycle Although endometriosis and adenomyosis are often regarded as variants of the same condition, it appears that adenomyosis usually occurs in an older age group (about ages 35 through 50) compared to endometriosis (about ages 15 through 50). In addition, adenomyosis is often associated with heavy menstrual bleeding which is usually not the case for endometriosis. Finally, the surgical option for the treatment of adenomysosis is mainly limited to hysterectomy while conservative surgery aiming at excising endometriosis lesions is widely applied for endometriosis and hysterectomy per se is of no benefit unless associated with ovariectomy. Moreover, the efficacy of standard treatment for endometriosis is of limited benefit in adenomyosis.

About 10% of women with adenomyosis have also had endometriosis in other sites such as the pelvic wall, ovaries, fallopian tubes etc. . . .

Although adenomyosis and endometriosis are often considered related, they are nevertheless two different conditions.

In 2008, Templeman et al. (Vol. 90, No. 2, August 2008 in Fertility and Sterility) demonstrated axes of differentiation between adenomyosis and endometriosis, among which notably the "age" criteria. The authors demonstrated that "Women diagnosed with endometriosis were younger than those diagnosed with adenomyosis."

Vavilis D et al. described in a study to estimate the frequency and risk factors for adenomyosis that "no relationship was found between adenomyosis and endometriosis". (Clin Exp Obstet Gynecol. 1997; 24(1):36-8.).

Vercelleni et al. (Best Practice & Research Clinical Obstetrics & Gynaecology Volume 20, Issue 4, Pages 465-477, August 2006) came to the conclusion, in a study related to adenomyosis epidemiological factors, that "no significant association has been demonstrated between adenomyosis and endometriosis. The two conditions have different epidemiological characteristics. These findings suggest that the two disorders are different clinical and nosological entities with no shared aetiological mechanisms."

As it was demonstrated, endometriosis and adenomyosis are two distinct conditions, with no shared aetiological mechanisms and moreover affecting different categories of populations. This could suggest that method of treatment for boths indication could differ as a treatment appropriate for endometriosis might not be indicated and appropriate for the treatment of adenomyosis.

Surprisingly, Applicants have found that administering a daily dosage of a therapeutically effective amount of ulipristal, or any metabolite thereof, to a patient suffering from, or afflicted with, endometriosis or endometriosis interna (adenomyosis) reduces pain associated with these conditions.

As used herein, a "therapeutically effective amount" is an amount effective, and also, safe, to ameliorate or prevent the symptoms, e.g. pain, bleeding, anemia.

Surprisingly enough, the Applicants have shown that the reduction of pain associated with endometriosis or adenomyosis is more important with therapeutically effective dose or amount of 5 mg to 12 mg of ulipristal, even more important with a dose of about 10 mg, compared to 5 mg. A dose of 10 mg per day is thus most preferred. A lower dosage is also contemplated, e.g. between 5 mg and 12 mg daily, preferably between 9 and 11 mg daily.

"Administering", as it applies in the present invention, refers to contact of ulipristal or any metabolite thereof, usually in the form of a therapeutically effective amount, to the patient, preferably a human, most preferably a female human.

Patients with endometriosis or adenomyosis may present with many different symptoms and severity. Most commonly this is dysmenorrhea, but inter-menstrual pain, dyspareunia, dyschezia, menorrhagia, and infertility are also part of the constellation of symptoms of endometriosis or adenomyosis. Usually, pain concerns chronic pelvic pain, pain before and during periods, pain with intercourse, low back pain, painful bowel movements (especially during menstruation) and painful urination during menstruation. Generally but not always, pain is associated with the degree of disease involvement.

As used herein, ulipristal (acetate), formerly known as CDB-2914, is 17α-acetoxy-11β-[4-N,N-dimethylaminophenyl)-19-norpregna-4,9-diene-3,20-dione. It is a well-known steroid, more specifically a 19-norprogesterone, which possesses antiprogestational and antiglucocorticoidal activity. This compound, and methods for its preparation, are described in U.S. Pat. Nos. 4,954,490, 5,073,548, and 5,929,262, and international patent applications WO2004/065405 and WO2004/078709. Properties of this compound are further described by Blithe et al, in Steroids, 2003 November; 68(10-13):1013-7.

An "active metabolite", as used herein, refers to a product produced through metabolism in the body of a specified compound or salt thereof and which exhibits the same biological activity as the specified compound. Active metabolites of ulipristal or of a salt thereof may be identified using routine techniques known in the art and their activities determined using tests such as those described herein. Such metabolites may result for example from the oxidation, reduction, hydrolysis, amidation, deamidation, esterification, deesterification, enzymatic cleavage, and the like, of the administered ulipristal or of a salt thereof. Accordingly, the invention includes active metabolites of ulipristal or of a salt thereof, including compounds produced by a process comprising contacting a compound of this invention with a mammal for a period of time sufficient to yield a metabolic product thereof. Such metabolite may also be produced in vitro by oxidation, reduction, hydrolysis, amidation, deamidation, esterification, deesterification, or enzymatic cleavage of the corresponding ulipristal or salt thereof.

Examples of metabolites of ulipristal (CDB-2914), include those described in Attardi et al, 2004, e.g. monodemethylated CDB-2914 (CDB-3877); didemethylated CDB-2914 (CDB-3963); 17 alpha-hydroxy CDB-2914 (CDB-3236); aromatic A-ring derivative of CDB-2914 (CDB-4183).

Ultipristal, or a metabolite thereof, may be administered by any convenient route, including oral, buccal, sublingual, parenteral, transdermal, vaginal, rectal, etc.

For a brief review of present methods for drug delivery, see, Langer, Science 249:1527-1533 (1990), which is incorporated herein by reference. Methods for preparing administrable compounds are known or are apparent to those skilled in the art and are described in more detail in, for example, Remington's Pharmaceutical Science, 17th Ed., Mack Publishing Company, Easton, Pa. (1985), which is incorporated herein by reference, and which is hereinafter referred to as "Remington".

Unit dosages of immediate-release formulations are preferred.

For solid compositions, conventional nontoxic solid carriers may be used which include, for example, pharmaceutical grades of mannitol, lactose, starch, magnesium stearate, sodium saccharine, talcum, cellulose, glucose, sucrose. For oral administration, a pharmaceutically acceptable nontoxic composition is formed by incorporating any of the normally employed excipients, such as those carriers previously listed.

The mode of administration possibilities include tablets, capsules, lozenges, pills, transdermal patches, dental pastes, suppositories, inhalants, sprays, intranasal delivery systems, solutions, ointments, parenteral depots, vaginal rings, vaginal gels and intra-uterine delivery systems.

Oral solid dosage forms are preferentially compressed tablets or capsules. Compressed tablets may contain diluents to increase the bulk of the ulipristal (CDB-2914), or a metabolite thereof, so that production of a compressed tablet of practical size is possible. Binders, which are agents which impart cohesive qualities to powdered materials may be also necessary. Povidone, starch, gelatin, sugars such as lactose or dextrose, and natural and synthetic gums may be used. Disintegrants are generally necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion of the tablet material to surfaces in the manufacturing process and to improve the flow characteristics of the powder material during manufacture. Colloidal silicon dioxide is most commonly used as a glidant and compounds such as talc, magnesium stearate or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of the progestogen agent or progesterone receptor modulator and inert ingredients. Procedures for production and manufacture of hard gelatin and soft elastic capsules are well known in the art (See Remington).

The oral route is preferred. Other routes of administration can be suitable in comparison with oral routes using blood levels to provide clinical success.

In cases where ulipristal, or a metabolite thereof, is included in a solution, the formulation may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Useful intranasal formulations of ulipristal, or a metabolite thereof, may contain a stabilizer and a surfactant. Among the pharmaceutically acceptable surfactants are polyoxyethylene castor oil derivatives, such as polyoxyethylene-glycerol-triricinoleate, also known as polyoxyl 35 caster oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) (all available from ICI Surfactants of Wilmington, Del.); polyglyceryl esters, such as polyglyceryl oleate; and polyoxyethylated kernel oil (LABRAFIL, available from Gattefosse Corp.). Preferably, the surfactant will be between about 0.01% and 10% by weight of the pharmaceutical composition. Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition.

Suspensions may also include chelating agents such as ethylene diamine tetraacetic acid, its derivatives and salts thereof, dihydroxyethyl glycine, citric acid and tartaric acid among others. Additionally, proper fluidity of a suspension can be maintained, for example, by the use of coating materials such as lecithin, by the maintenance of the required particle size in the case of dispersions and by the use of surfactants, such as those previously mentioned. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay; and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Preferably the amount of ulipristal or a metabolite thereof is effective to alleviate pain associated with endometriosis or adenomyosis without clinically significant antiglucocorticoid activity.

According to this invention, ulipristal or a metabolite thereof will be administered, preferably daily, by oral route for a period of 1 to up to 120 days, preferably up to 91 days (13 weeks). During this treatment period, the administration can be stopped if the patient considers that pain associated with adenomyosis or endometriosis is reduced. A course of treatment as described above can be repeated as needed 2 to 3 time per year, as long as at least one spontaneous menstruation is allowed to occur between two treatment courses.

This invention also envisages the use of ultipristal, or a metabolite thereof, in a pharmaceutically acceptable salt form. Non-limiting examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like. Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, pamoic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Alternatively, or additionally, it will become apparent that ulipristal, or a metabolite thereof, may be administered alone or in combination with other treatments, therapeutics or agents, either simultaneously or sequentially dependent upon the condition to be treated. For example, ulipristal, or a metabolite thereof, in the method of the invention may be administered in association with a pain killer or iron and/or sequentially with a progesterone.

Also with in the scope of the present invention is a method for reducing or stopping bleeding in a patient afflicted with dislocation of the endometrium (endometriosis or adenomyosis) comprising administering to said patient in need thereof, a daily dosage of 5 mg to 12 mg of ulipristal, or any metabolite thereof. As shown in examples 1 and 2, at the end of the treatment patients treated with Ulipristal at a daily dose of 5 mg or 10 mg, had a PBAC score which corresponds to amenorrhea.

Further encompassed in the present invention is a method for preventing or treating anemia in a patient afflicted with dislocation of the endometrium (endometriosis or adenomyosis), comprising administering to said patient in need thereof, a daily dosage of 5 mg to 12 mg of ulipristal, or any metabolite thereof, alone or in combination with e.g. iron. As exemplified in the present application, the levels of Hb of patients treated with Ulipristal at a daily dose of 5 mg or 10 mg had increased during the treatment (documenting correction of anemia), regardless whether these patients were concomitantly treated with iron or not The invention further provides a method for reducing uterine volume in a patient afflicted with dislocation of the endometrium (endometriosis or adenomyosis), comprising administering to said patient in need thereof, a daily dosage of 5 mg to 12 mg of ulipristal, or any metabolite thereof. Examples 1 and 2 have shown that patients undergoing treatment with Ulipristal at a daily dose of 5 mg or 10 mg had a decrease in uterine volume at the end of their treatment.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Effect of 5 Mg and 10 Mg Ulipristal Therapy on Adenomyosis

1. Clinical Study

A double-blinded, randomized, placebo-controlled study evaluating the effect of long term (13 weeks) oral administration of 5 mg or 10 mg ulipristal in patients with heavy menstrual bleeding and pain included 5 patients who had adenomyosis.

These patients included women 36 years of age or older diagnosed by MRI with adenomyosis but no evidence of uterine fibroid.

The patients were randomized as follows: 1 patient received a daily placebo treatment (matching Esmya tablet appearance) and iron 80 mg/day, 2 patients received a daily dose of 5 mg ulipristal (Esmya®) and iron 80 mg/day and 2 patients received a daily dose of 10 mg ulipristal (Esmya®) and iron 80 mg/day for 13 weeks.

2. Parameters Assessed

Different parameters were assessed before treatment (Baseline) and after the end of treatment (13 weeks):

The PBAC score (Pictorial Blood Loss Assessment Chart) gives an estimation of the menstrual blood loss. This score was measured before treatment and continuing up to week 13 of treatment. Normal menstrual bleeding score is <75. Abnormal bleeding (menorrhagia) is characterized by a PBAC score >100. Higher the score, worse is the bleeding.

The Uterine volume was estimated before treatment (Baseline Uterine volume) and the % change in uterine volume was reported at the end of the treatment (week 13).

The SF-M P QPart A (short form of the Mc Gill Pain questionnaire) was used as a measure of the sensory, affective and intensity dimensions of pain. The pain was estimated before treatment and the change was reported at the end of the treatment (week 13). (NOTE: The lowest is the score, the better it is).

The SF-MPQ Part B (short form of the Mc Gill Pain questionnaire) wherein the pain is assessed with a visual analogue scale (VAS) before treatment and the change was reported at the end of the treatment (week 13). (NOTE: The lowest is the score, the better it is).

Discomfort questionnaire (disease specific quality of life questionnaire) estimating the quality of life before treatment and the change was reported at the end of the treatment (week 13). (NOTE: The lowest is the score, the better it is).

The level of Hb (Hemoglobin) was measured before treatment and at the end of the treatment. (NOTE: the higher it is, the better it is.)

3. Results

The results are shown in Table 1.

TABLE 1

| Ulipristal Dose | 0 | 5 mg | 5 mg | 10 mg | 10 mg |
|---|---|---|---|---|---|
| Patient No | 126/1384 | 130/1368 | 142/1036 | 148/1427 | 154/1240 |
| Age (years) | 45 | 41 | 48 | 36 | 48 |
| Baseline PBAC | 186 | 232 | 994 | 624 | 536 |
| PBAC at week 13 | 273 | 0 | 0 | 0 | 0 |
| Change in PBAC | +87 | −232 | −994 | −624 | −536 |
| Baseline Uterine volume | 208.7 | 338.5 | 210.9 | 364.8 | 161.6 |
| % change in uterine volume at week 13 | +9.5% | −21.5% | +0.4% | 36.4% | −32.0% |
| Baseline SF-MPQ Part A | 27 | 6 | 1 | 3 | 14 |
| Change at Week 13 | −14 | −5 | 0 | −2 | −14 |
| Baseline SF-MPQ Part B (VAS) | 50 | 11 | 31 | 48 | 93 |
| Change at Week 13 | +25 | −7 | −6 | −43 | −93 |
| Discomfort questionnaire Baseline | 15 | 8 | 11 | 21 | 14 |
| Change at Week 13 | −1 | −5 | −9 | −20 | −12 |
| Baseline Hb (g/dL) | 9.6 | 10 | 9.4 | 9.1 | 9.1 |
| Hb at Week 13 | 13.9 | 13.5 | 14 | 13.6 | 12.1 |
| Surgery | laparatomic hysterectomy | no surgery | no surgery | laparatomic hysterectomy | no surgery |

3.1 All four ulipristal treated patients had improvements in pain compared to the placebo treated patient as measured with the SF-MPQ Part B (VAS). Patients treated at 10 mg ulipristal had better pain relief compared to patients that received 5 mg ulipristal. Very substantial improvement in pain was observed at 10 mg ulipristal for both patients and complete absence of pain was observed for one of these patients.

3.2 All 4 patients treated with 5 mg or 10 mg of ulipristal had PBAC score of 0 at the end of treatment (week 13) (i.e. no bleeding at all=amenorrhea) whereas the placebo treated patient had an increase in menstrual blood loss at week 13 (change +87).

3.3 The % change in uterine volume at week 13 for the ulipristal treated patients was +36.4% for one patient, and was +0.4%, −21.5% and −32% for the other patients. The placebo treated patient had a % change in uterine volume at week 13 of +9.5%. Among the 4 patients treated with ulipristal, two of them had a decrease of the uterine volume compared to the placebo treated patient.

3.4 All four patients had substantial improvement in the quality of life compared to the placebo treated patient.

3.5 The levels of Hb revealed that all four ulipristal treated patients as well as the placebo treated patient had an increase in Hb at the end of the treatment consistent with the fact that all patients received concomitant iron therapy (1 tablet of 80 mg or iron once daily, Tardyferon®) and the absence of blood loss of the patients treated with ulipristal acetate at week 13. However, the same results have been observed in patients treated only with ulipristal.

Example 2

Effect of 5 Mg and 10 Mg Ulipristal Therapy on Pain in Patient with Adenomyosis or Endometriosis 1. Clinical Study A double-blinded, randomized, study evaluating the effect of long term oral administration of 5 mg or 10 mg ulipristal in patients with heavy menstrual bleeding and pain.

The control group consisted of patients treated with GnRH agonist.

These patients included women 36 years of age or older with evidence of uterine fibroids and adenomyosis or endometriosis diagnosed by ultrasound.

Patient 210/5252 (candidate having adenomyosis) received a daily dose of 5 mg ulipristal (Esmya®) for 13 weeks and was followed up to week 38. A myomectomy by laparotomy was conducted after Week 13 visit.

Patient 281/5214 (candidate having endometriosis) received a daily dose of 5 mg ulipristal (Esmya®) for 13 weeks and was followed up to week 38.

Patient 210/5095 (candidate having adenomyosis) received a daily dose of 10 mg ulipristal (Esmya®) for 13 weeks and was followed up to week 38. A hysterectomy by laparoscopy was conducted after Week 13 visit.

Patient 210/5308 (candidate having endometriosis) received a daily dose of 10 mg ulipristal (Esmya®) for 13 weeks and was followed up to week 38. A myomectomy by hysteroscopy was conducted after Week 13 visit.

A myomectomy by laparoscopy and hysteroscopy was conducted between Week 26 & 38 visits.

Patient 250/5090 (candidate having endometrioma) received a daily dose of 10 mg ulipristal (Esmya®) for 13 weeks and was followed up to week 38.

2. Results

The results are shown in Table 2 below 2.1 All four ulipristal treated patients (281/5214, 210/5095, 210/5308, 250/5090) showed an improvement in pain at week 5, 9, 13th compared to baseline. Data obtained for patient 210/5095 are particularly relevant: starting from $5^{th}$ week the patient experienced no pain anymore and starting from week 9, she even did not bleed anymore.

This is the demonstration of ulipristal efficacy in pain and bleeding reduction in patient suffering from adenomyosis and uterine fibroids with results comparable to surgery.

2.2 All 3 patients (281/5214, 210/5095, 250/5090) treated with 5 mg or 10 mg of ulipristal had PBAC score of 0 (amenorrhea) at the end of treatment (week 13), whereas the placebo (example 1) treated patient had an increase in menstrual blood loss at week 13 (change +87). Patient 210/5308, had a PBAC value of 55 at week 13 which is considered as normal menstrual bleeding (normal menstrual bleeding PBAC is <75).

TABLE 2

| UPA | patient | Age (yrs) | Visit | A(SF-MPQ) Score+ | A(SF-MPQ) CFB+ | B(VAS) Score | B(VAS) CFB+ | PBAC Score | PBAC CFB+ | Uterine Volume (cm3) | % Change in Uterine Volume |
|---|---|---|---|---|---|---|---|---|---|---|---|
| 5 mg | 210/5252 | 37 | Baseline | 12 | | 43 | | 225 | | 236.1 | |
| | | | Week 5 | 14 | −2 | 64 | 21 | 375 | 150 | | |
| | | | week 9 | 11 | −1 | 57 | 14 | 283 | 58 | | |
| | | | Week 13 | 9 | −3 | 37 | −6 | 124 | −101 | 251.7 | 6.6 |
| | | | Week 17 | | | | | NA | | | |
| | | | Week 26 | 8 | −4 | 67 | 24 | 755 | 530 | | |
| | | | Week 38 | 9 | −3 | 70 | 27 | 271 | 46 | | |
| | | | Myomectomy by laparotomy after Week 13 visit | | | | | | | | |
| 5 mg | 281/5214 | 49 | Baseline | 4 | | 20 | | 220 | | 131.1 | |
| | | | Week 5 | 1 | −3 | 3 | −17 | 46 | −174 | | |
| | | | week 9 | 0 | −4 | 0 | −20 | 0 | −220 | | |
| | | | Week 13 | 0 | −4 | 0 | −20 | 0 | −220 | 159.1 | 21.3 |
| | | | Week 17 | | | | | NA | | 147.7 | 12.6 |
| | | | Week 26 | | | 73 | 53 | 52 | −168 | 102.2 | −21.2 |
| | | | Week 38 | 0 | −4 | 0 | −20 | 571 | 351 | 98.9 | −24.6 |
| | | | No Surgery | | | | | | | | |
| 10 mg | 210/5095 | 49 | Baseline | 14 | | 88 | | 860 | | 368.5 | |
| | | | Week 5 | 0 | 14 | 0 | −88 | 328 | −532 | | |
| | | | week 9 | 0 | 14 | 0 | −88 | 0 | −860 | | |
| | | | Week 13 | 0 | −14 | 0 | −88 | 0 | −860 | 284.7 | −33.8 |
| | | | Week 17 | 0 | −14 | | | NA | | | |
| | | | Week 26 | 0 | −14 | 0 | −88 | 0 | | | |
| | | | Week 38 | 0 | −14 | 0 | −88 | | | | |
| 5 mg | 210/5252 | 37 | Baseline | 12 | | 43 | | 225 | | 236.1 | |
| | | | Week 5 | 14 | −2 | 64 | 21 | 375 | 150 | | |
| | | | week 9 | 11 | −1 | 57 | 14 | 283 | 58 | | |
| | | | Week 13 | 9 | −3 | 37 | −6 | 124 | −101 | 251.7 | 6.6 |
| | | | Week 17 | | | | | NA | | | |
| | | | Week 26 | 8 | −4 | 67 | 24 | 755 | 530 | | |
| | | | Week 38 | 9 | −3 | 70 | 27 | 271 | 46 | | |
| | | | Myomectomy by laparotomy after Week 13 visit | | | | | | | | |
| 5 mg | 281/5214 | 49 | Baseline | 4 | | 20 | | 220 | | 131.1 | |
| | | | Week 5 | 1 | −3 | 3 | −17 | 46 | −174 | | |
| | | | week 9 | 0 | −4 | 0 | −20 | 0 | −220 | | |
| | | | Week 13 | 0 | −4 | 0 | −20 | 0 | −220 | 159.1 | 21.3 |
| | | | Week 17 | | | | | NA | | 147.7 | 12.6 |
| | | | Week 26 | | | 73 | 53 | 52 | −168 | 102.2 | −21.2 |
| | | | Week 38 | 0 | −4 | 0 | −20 | 571 | 351 | 98.9 | −24.6 |
| | | | No Surgery | | | | | | | | |
| 10 mg | 210/5095 | 49 | Baseline | 14 | | 88 | | 860 | | 368.5 | |
| | | | Week 5 | 0 | 14 | 0 | −88 | 328 | −532 | | |
| | | | week 9 | 0 | 14 | 0 | −88 | 0 | −860 | | |
| | | | Week 13 | 0 | −14 | 0 | −88 | 0 | −860 | 284.7 | −33.8 |
| | | | Week 17 | 0 | −14 | | | NA | | | |
| | | | Week 26 | 0 | −14 | 0 | −88 | 0 | | | |
| | | | Week 38 | 0 | −14 | 0 | −88 | | | | |

2.3 Among the 4 patients, 3 patients (210/5095, 210/5308, 250/5090) had a decrease in uterine volume at week 13 compared to baseline.

Example 3

Ulipristal Liver Toxicity Analysis

1. Clinical Study

A double-blinded, randomized, study evaluating the effect of long term oral administration of 5 mg or 10 mg ulipristal in patients with heavy menstrual bleeding and pain.

A Hepatobiliary Disorders and Liver Safety analysis was carried out for all patients.

A summary of out of range values for biochemistry parameters is provided in table 4.

This summary table illustrates the increased number of subjects from the 3 treatment groups who had increased levels of AST, ALT and total bilirubin during the study.

The data are included in table 3 below:

TABLE 3

Summary of Biochemistry Out of Normal Range (Safety Population)

| Laboratory Parameter | On-Treatment Status | Week | Ulipristal 5 mg (n = 97) | Ulipristal 10 mg (n = 103) | GnRH-agonist (N = 101) |
|---|---|---|---|---|---|
| AST | Baseline (visit normal) | | 95 (97.9%) | 100 (97.1%) | 97 (96.0%) |
| | High not CS | 5 | 6 (6.2%) | 6 (5.8%) | 2 (2.0%) |
| | | 9 | 3 (3.1%) | 3 (2.9%) | 9 (8.9%) |
| | | 13 | 2 (2.1%) | 4 (3.9%) | 3 (3.0%) |
| | | 17 | 3 (3.1%) | 4 (3.9%) | 3 (3.0%) |
| | Low not CS | 5 | 0 | 0 | 0 |
| | | 9 | 0 | 0 | 0 |
| | | 13 | 0 | 0 | 0 |
| | | 17 | 0 | 0 | 0 |
| ALT | Baseline visit (normal) | | 94 (96.9%) | 100 (97.1%) | 98 (97.0%) |
| | High not CS | 5 | 4 (4.1%) | 6 (5.8%) | 3 (3.0%) |
| | | 9 | 0 | 3 (2.9%) | 5 (5.0%) |
| | | 13 | 1 (1.0%) | 5 (4.9%) | 6 (5.9%) |
| | High not CS | 17 | 2 (2.1%) | 4 (3.9%) | 3 (3.0%) |
| | High CS | 17 | 0 | 0 | 1 (1.0%) |
| | Low not CS | 5 | 0 | 0 | 0 |
| | | 9 | 0 | 0 | 0 |
| | | 13 | 0 | 0 | 0 |
| | | 17 | 0 | 0 | 0 |
| Total bilirubin | Baseline visit (normal) | | 92 (94.8%) | 102 99.0%) | 98 (97.0%) |
| | High not CS | 5 | 2 (2.1%) | 3 (2.9%) | 0 |
| | High CS | 5 | 0 | 0 | 1 (1.0%) |
| | High not CS | 9 | 3 (3.1%) | 4 (3.9%) | 1 (1.0%) |
| | | 13 | 3 (3.1%) | 6 (5.8%) | 2 (2.0%) |
| | | 17 | 2 (2.1%) | 2 (1.9%) | 2 (2.0%) |
| | Low not CS | 5 | 0 | 0 | 0 |
| | | 9 | 0 | 0 | 0 |
| | | 13 | 0 | 0 | 0 |
| | | 17 | 0 | 0 | 0 |

AST—aspartate transaminase, ALT—alanine transaminase, CS—clinically significant.

2. Results

Mildly elevated transaminase levels, were reported for a few subjects from all 3 treatment groups; in general the elevations were less than 2× upper limit of normal range (ULN), transient and resolved under treatment. Elevated transaminase levels were not accompanied by increased bilirubin levels. Four subjects (1 subject from each of the Ulipristal 5 mg and GnRH-agonist groups and 2 subjects from the Ulipristal 10 mg group), had elevations of both AST and ALT above 2×ULN, but <3×ULN for consecutive samples during the study. One subject from the GnRH-agonist group had raised direct, indirect and total bilirubin levels throughout the study, which were not accompanied by raised transaminase levels.

In summary, there were no signals of any treatment related changes in liver function tests.

In addition, the Hepatobiliary Disorders and Liver Safety analysis revealed no evidence of liver toxicity based on the Treatment Emergent Adverse Events (TEAEs) reported in the clinical studies.

The invention claimed is:

1. A method for the treatment of pain associated with dislocation of the endometrium in a patient, comprising administering ulipristal or a metabolite thereof selected from the group consisting of CDB-3877, CDB-3963, CDB-3236, and CDB-4183 to the patient in need thereof,
   wherein said ulipristal, or said metabolite thereof, is administered at a daily dosage of about 5 to 12 mg,
   wherein the dislocation of the endometrium results in adenomyosis or endometriosis, and
   wherein the pain is chronic pelvic pain, pain with intercourse, low back pain, painful bowel movements, painful urination during menstruation, or a combination thereof.

2. The method of claim 1, wherein the method comprises administering a tablet comprising the ulipristal or the metabolite thereof to the patient.

3. The method of claim 1, wherein the daily dosage of ulipristal, or the metabolite thereof, is about 5 mg.

4. The method of claim 1, wherein the daily dosage of the ulipristal, or the metabolite thereof, is about 10 mg.

5. The method of claim 1, wherein the ulipristal or the metabolite thereof is administered for a period of 1 to up to 120 days.

6. The method of claim 1, wherein the painful bowel movements is during menstruation.

7. The method of claim 1, wherein the ulipristal or the metabolite thereof is administered for about 13 weeks.

\* \* \* \* \*

UNITED STATES PATENT AND TRADEMARK OFFICE
CERTIFICATE OF CORRECTION

PATENT NO.         : 10,441,593 B2
APPLICATION NO.    : 13/976895
DATED              : October 15, 2019
INVENTOR(S)        : Loumaye et al.

Page 1 of 1

It is certified that error appears in the above-identified patent and that said Letters Patent is hereby corrected as shown below:

In the Claims

In Column 14, Claim 1, Line 13, delete "endometriumin" and insert -- endometrium in --, therefor.

Signed and Sealed this
Twenty-first Day of April, 2020

Andrei Iancu
*Director of the United States Patent and Trademark Office*